(12) United States Patent
Josselin et al.

(10) Patent No.: US 11,632,169 B2
(45) Date of Patent: Apr. 18, 2023

(54) METHOD FOR SYNCHRONIZING A MAGNETIC LOCATING SYSTEM (71) Applicant: Commissariat a l'energie atomique et aux energies alternatives, Paris (FR)

(72) Inventors: Vincent Josselin, Grenoble (FR); Francois Bertrand, Seyssins (FR); Saifeddine Aloui, Grenoble (FR); Jerome Paulet, Valence (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 1168 days.

(21) Appl. No.: 16/158,690

(22) Filed: Oct. 12, 2018

(65) Prior Publication Data

US 2019/0113585 A1 Apr. 18, 2019

(30) Foreign Application Priority Data

Oct. 13, 2017 (FR) ...................... 17 59637

(51) Int. Cl.
*H04B 7/26* (2006.01)
*G01R 33/00* (2006.01)
(Continued)

(52) U.S. Cl.
CPC ....... *H04B 7/2678* (2013.01); *G01R 33/0023* (2013.01); *G01R 33/02* (2013.01);
(Continued)

(58) Field of Classification Search
CPC . G06F 1/12; G06F 1/08; H04L 7/0012; H04L 7/0016; H04B 7/2678; G01R 33/0023; G01R 33/02; H04J 3/0667
(Continued)

(56) References Cited

U.S. PATENT DOCUMENTS 6,188,355 B1 2/2001 Gilboa
7,015,859 B2 3/2006 Anderson
(Continued)

OTHER PUBLICATIONS

French Preliminary Search Report dated Aug. 9, 2018 in French Application 17 59637, filed on Oct. 13, 2017 (with English Translation of Categories of Cited Documents & Written Opinion)
(Continued)

*Primary Examiner* — Ji H Bae
(74) *Attorney, Agent, or Firm* — Oblon, McClelland, Maier & Neustadt, L.L.P.

(57) ABSTRACT

The method relates to a synchronization of a magnetic locating system including a first device and a second device each including an oscillator, a time counter clocked by the oscillator, and a radiocommunication module. The locating system also includes a device for emitting and receiving alternating magnetic fields, the device being configured to allow a propagation of alternating magnetic fields between the first and second devices, the device for emitting and receiving alternating magnetic fields being connected to the oscillators of the first and second devices. The synchronizing method includes a synchronizing step that is configured to synchronize the oscillators of the first and second devices by adjusting, by servo-controlling the oscillator of the second device, the operation of the time counter of the second device to the operation of the time counter of the first device.

17 Claims, 3 Drawing Sheets

(51) Int. Cl.
*G06F 1/12* (2006.01)
*G01R 33/02* (2006.01)
*H04J 3/06* (2006.01)
*H04L 7/00* (2006.01)
*G06F 1/08* (2006.01)

(52) U.S. Cl.
CPC .............. *G06F 1/12* (2013.01); *H04J 3/0667* (2013.01); *G06F 1/08* (2013.01); *H04L 7/0012* (2013.01); *H04L 7/0016* (2013.01)

(58) Field of Classification Search
USPC .............. 713/375, 500; 702/150; 324/207.17
See application file for complete search history.

(56) References Cited

U.S. PATENT DOCUMENTS

| | | | |
|---|---|---|---|
| 7,443,154 | B1 | 10/2008 | Merewether et al. |
| 7,733,077 | B1 | 6/2010 | Merewether et al. |
| 7,873,491 | B2 | 1/2011 | Higgins et al. |
| 8,013,595 | B2 | 9/2011 | Jones et al. |
| 8,106,660 | B1 | 1/2012 | Merewether et al. |
| 8,121,812 | B2 | 2/2012 | Higgins |
| 8,723,509 | B2 | 5/2014 | Patterson et al. |
| 9,411,066 | B1 | 8/2016 | Olsson et al. |
| 2004/0177162 | A1* | 9/2004 | Wetzel ................ H04L 29/06 709/248 |
| 2005/0165297 | A1 | 7/2005 | Anderson et al. |
| 2005/0285591 | A1 | 12/2005 | Higgins et al. |
| 2007/0226530 | A1* | 9/2007 | Celinski ................ G06F 1/12 713/500 |
| 2014/0002063 | A1 | 1/2014 | Ashe |
| 2016/0011013 | A1 | 1/2016 | Pedrotti et al. |
| 2016/0072883 | A1* | 3/2016 | Long .................. G06F 11/16 709/219 |
| 2016/0377451 | A1 | 12/2016 | Pedrotti et al. |
| 2017/0131424 | A1 | 5/2017 | Olsson |
| 2018/0053056 | A1* | 2/2018 | Rabinovich .......... G06K 9/4628 |
| 2019/0243472 | A1* | 8/2019 | Stafford .............. G02B 27/017 |

OTHER PUBLICATIONS

Raab, F., et al. "Magnetic Position and Orientation Tracking System", IEEE Transactions on Aerospace and Electronic Systems, vol. AES-15, No. 5, 1979, 10 pages.

* cited by examiner

METHOD FOR SYNCHRONIZING A MAGNETIC LOCATING SYSTEM

FIELD OF THE INVENTION

The field of the invention relates to the magnetic location of devices with respect to one another. More particularly, the invention relates to a method for synchronizing a magnetic locating system.

PRIOR ART

A magnetic locating system may be based on the modulation, notably amplitude modulation, of alternating magnetic fields, to determine a relative position and a relative orientation between a device comprising an emitter of alternating magnetic fields and a device comprising a receiver of alternating magnetic fields.

To establish a relative location between two devices, in particular at least one of the devices being movable with respect to the other, it is known to equip one of the devices with emitting coils and the other of the devices with receiving coils. The emitting coils allow alternating magnetic fields to be emitted the modulations of which are received by the receiving coils. Next, an analysis of the alternating magnetic fields received by the receiving coils with respect to data relating to the emitted alternating magnetic fields allows, via suitable demodulations and filtering, the relative location between the two devices to be determined. A relative location may correspond to a calculation of the position and orientation of one of the devices with respect to the other of the devices.

Patent application US 2005/0165297 describes an example of operation of a magnetic locating system.

The link between the two devices may be a wire link. In particular, with a wire link, a synchronous detection principle is used by the device receiving the alternating magnetic fields emitted by the device emitting the alternating magnetic fields, notably thanks to the use of a control signal emitted by the device emitting the alternating magnetic fields, which allows the reception of the alternating magnetic fields to be aligned temporally with the emission of the alternating magnetic fields: the emission and the reception are then triggered simultaneously. This is notably possible because of the presence of a central processor comprising a single oscillator synchronously controlling the emission and the reception of the alternating magnetic fields.

One drawback of the wire link is the constraint relating to the physical link between the two devices, or between the two devices and a central processor, which may for example limit the movements between the two devices. There is therefore a need to remove the constraint of a wire link, for example, in order to allow better ergonomics/flexibility in use of the magnetic locating system.

However, removing the wiring constraint is not so simple. Specifically, the removal of the wire link actually removes the common time reference between the two devices, each of these devices then operating with independent oscillators. This naturally results in a drawback caused by a phase ambiguity in the process of demodulating the magnetic fields received by the device receiving the alternating magnetic fields, ambiguity that it is necessary to remove if it is desired to correctly estimate the orientation and direction of the received magnetic fields, and therefore to correctly estimate a location of one of the devices of the locating system with respect to the other of the devices of the locating system. There are a number of ways of overcoming this synchronization problem.

One solution, proposed by patent U.S. Pat. No. 8,121,812, is to implement time multiplexing of the emitted magnetic fields, which is composed of three emission windows and one synchronization window. The frequencies of the emitted magnetic fields are moreover constrained: the duration of the emission windows must correspond to an integer multiple of the period of each emitted magnetic field. This solution has the drawback of limiting the frequencies used to implement the magnetic location and of on the whole slowing down the magnetic locating system related to the time multiplexing of the magnetic fields. Moreover, this solution also has the drawback of limiting phase-ambiguity removal to within $\pi$, this not allowing a phase shift, sign of a presence of a potential artefact hindering the magnetic location, to be detected. An artefact corresponds to an exterior perturbator of the alternating magnetic fields.

Patent application US 2016/0011013 proposes a solution for removing the phase ambiguity by synchronization of an emitter and a receiver of magnetic fields. To do this, this patent application US 2016/0011013 proposes a synchronization allowing a piece of phase information to be initially derived from known information. Next, this piece of phase information is tracked and updated assuming that there is a correlation between the signals of the receiver from one measurement to the next. This solution has various drawbacks:

- it requires an initial calibration by learning on the basis of known positions,
- if the signal is lost during the magnetic location, it is necessary to carry out the calibration phase again, and
- the ambiguity of the phase is limited to within $\pi$, this making it difficult to apply artefact-detection methods based on fine analysis of the phases of the received magnetic fields.

There is therefore a need to develop a solution, notably one that is more robust in case of signal loss, allowing a better removal of phase ambiguity, i.e. one that is preferably not limited to within $\pi$.

OBJECT OF THE INVENTION

The invention aims to remedy all or some of the aforementioned drawbacks. Notably, the aim of the invention is to propose a synchronization that in particular makes it possible to keep identical the phases and frequencies of the modulations of emitted alternating magnetic fields with reference signals serving for the demodulation of the received alternating magnetic fields, in order to implement a magnetic location.

To this end, one object of the invention relates to a method for synchronizing a magnetic locating system, the magnetic locating system comprising:

- a first device and a second device each comprising an oscillator, a time counter clocked by said oscillator, and a radiocommunication module, and
- a device for emitting and receiving alternating magnetic fields, said device being configured to allow a propagation of alternating magnetic fields between the first and second devices, said device for emitting and receiving alternating magnetic fields being connected to the oscillators of the first and second devices, this synchronizing method comprising a synchronizing step configured to synchronize the oscillators of the first and second devices by adjusting, by servo-controlling the oscillator of the second device, the operation of the time counter of the second device to the operation of the time counter of the first device.

The synchronizing method may comprise one or more of the following features:
- the synchronizing step comprises:
  - a step of transmitting first timestamps, determined by the time counter of the first device, to the second device by radiocommunication between the radiocommunication modules of the first and second devices,
  - a step of determining second timestamps by the time counter of the second device,
  - a step of determining second timestamps by the time counter of the second device, and
- the synchronizing step comprises the radiocommunication module of the first device emitting synchronization signals to the radiocommunication module of the second device, each of the first timestamps being transmitted by one of the synchronization signals, and each time a synchronization signal is emitted by the radiocommunication module of the first device:
  - one of the first timestamps to be transmitted by a synchronization signal consecutive to said emitted synchronization signal is determined by the time counter of the first device,
  - one of the first timestamps to be transmitted by a synchronization signal consecutive to said emitted synchronization signal is determined by the time counter of the first device, and
- the servo-controlling step comprises steps of determining a servo-control setpoint of the oscillator of the second device each followed by a step of applying said servo-control setpoint, each servo-control setpoint being determined using a time differential taking into account one of the first timestamps and one the second timestamps;
- the servo-controlling step comprises steps of determining a servo-control setpoint of the oscillator of the second device each followed by a step of applying said servo-control setpoint, each servo-control setpoint being determined using a time differential taking into account one of the first timestamps and one of the second timestamps, corresponding to a timestamp of the emission and to a timestamp of the reception of the same synchronization signal, respectively;
- each step of determining a servo-control setpoint of the oscillator of the second device is triggered by the reception of one of the synchronization signals, and the synchronization signals are emitted at regular intervals so as to allow the application of the determined servo-control setpoint between the reception of the synchronization signal that triggered its determination and the reception of a consecutive synchronization signal;
- each synchronization signal received by the radiocommunication module of the second device, and for which the second device has available one of the second timestamps determined by the time counter of the second device on the reception of a synchronization signal preceding said received synchronization signal, causes the implementation of one of the steps of determining a servo-control setpoint for which the time differential is obtained while taking into account:
  - one of the first timestamps, which is extracted from said received synchronization signal, and
  - said second timestamp determined by the time counter of the second device on the reception of said synchronization signal preceding said received synchronization signal;
- the step of servo-controlling the oscillator of the second device comprises use of a loop filter;
- the loop filter implements a proportional-integral control law; and
- each servo-control setpoint is a control voltage of the oscillator of the second device.

The invention also relates to a magnetic locating method comprising a step of implementing the synchronizing method such as described, and a step of finding the relative location between the first and second devices while taking into account data from the device for emitting and receiving alternating magnetic fields.

The magnetic locating method may comprise one or more of the following features:
- the magnetic locating method comprises, after adjustment of the operation of the time counter of the second device to the operation of the time counter of the first device, a step of comparing a time setpoint with data from the time counters of the first and second devices, and the magnetic locating method comprises a step of starting up the device for emitting and receiving alternating magnetic fields, said step being triggered depending on the result of the comparing step;
- the device for emitting and receiving alternating magnetic fields comprises an emitter of alternating magnetic fields and a receiver of alternating magnetic fields, and the magnetic locating method comprises, after synchronization of the oscillators of the first and second devices:
  - a step of activating the emitter of alternating magnetic fields, said emitter being clocked by one of the oscillators of the first and second devices, this resulting in the emission of alternating magnetic fields, and
  - a step of activating the receiver of alternating magnetic fields, said receiver being clocked by the other of the oscillators of the first and second devices,
    - the steps of activating the receiver and emitter of alternating magnetic fields being triggered simultaneously using a time setpoint compared, on the one hand, to an output datum of the time counter of the first device, and, on the other hand, to an output datum of the time counter of the second device; and
- the synchronizing step is triggered before the emitter and receiver are activated, and is kept active during the operation of the emitter and receiver.

The invention also relates to a magnetic locating system comprising:
- a first device and a second device each comprising an oscillator, a time counter clocked by said oscillator, and a radiocommunication module, and
- a device for emitting and receiving alternating magnetic fields, said device being configured to allow a propagation of alternating magnetic fields between the first and second devices, said device for emitting and receiving alternating magnetic fields being connected to the oscillators of the first and second devices,
the locating system being configured so as to allow a synchronization of the oscillators of the first and second devices by adjustment, by servo-controlling the oscillator of the second device, of the operation of the time counter of the second device to the operation of the time counter of the first device.

BRIEF DESCRIPTION OF THE DRAWINGS

Other advantages and features will become more clearly apparent from the following description of particular embodiments of the invention, which are given by way of nonlimiting example and shown in the appended drawings, in which.

In these figures, the same references have been used to reference elements that are the same.

DESCRIPTION OF PARTICULAR EMBODIMENTS

One object of the invention relates to a method for synchronizing a magnetic locating system allowing two separate oscillators that will be used to clock a device for emitting and receiving alternating magnetic fields to be synchronized, these alternating magnetic fields being intended to be used to determine a relative location between the first and second devices of the magnetic locating system that will be described in more detail below.

Figure 1:
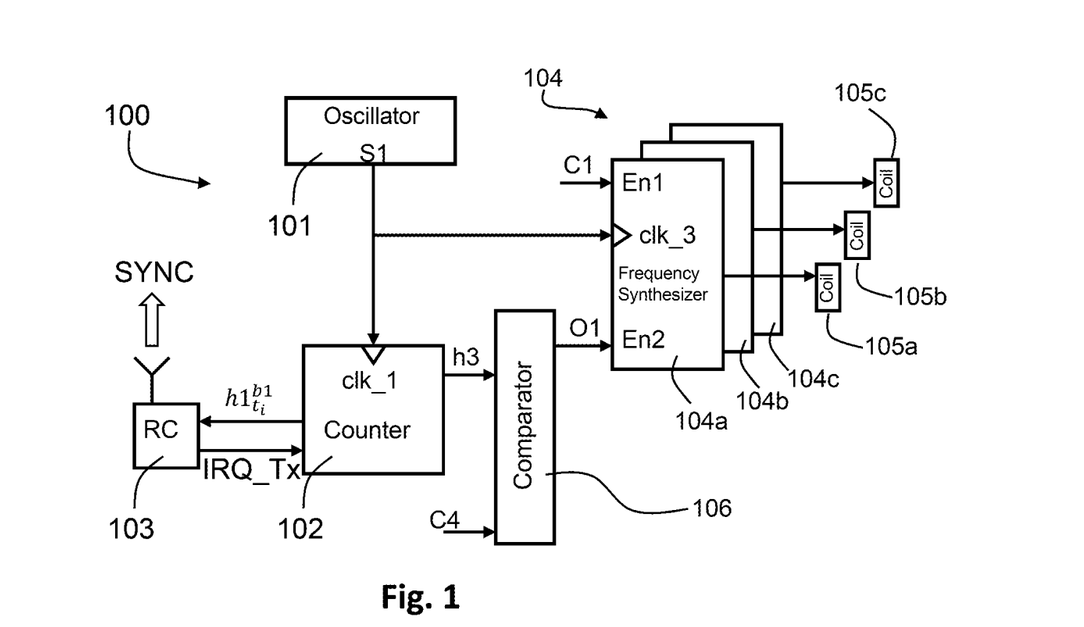
FIG. 1 shows one embodiment of the first device of a magnetic locating system, preferably intended to emit alternating magnetic fields in order to allow a relative location between the first device and a second device.
Figure 2:
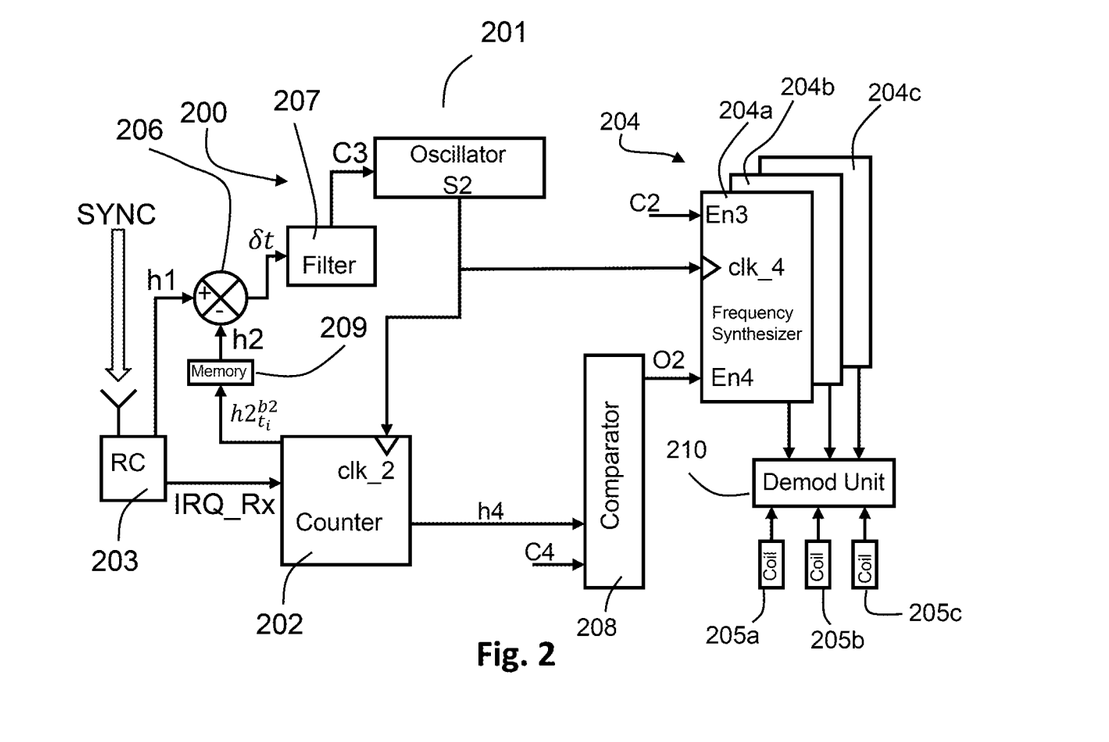
FIG. 2 shows one embodiment of the second device of the magnetic locating system, preferably intended to receive alternating magnetic fields that will be emitted by the first device in order to allow the relative location between the first device and the second device.

Notably, parts of the magnetic locating system are illustrated in FIGS. 1 and 2. The magnetic locating system comprises a first device 100 (FIG. 1) and a second device 200 (FIG. 2). The magnetic locating system is configured to establish at least one relative location between the first and second devices 100, 200, notably from alternating magnetic fields that are propagated between the first and second devices 100, 200. In other words, data from the, i.e. relating to the, alternating magnetic fields, which are notably emitted and received, may be used/taken into account in order to allow a relative location between the first and second devices 100, 200 to be determined.

By "relative location between the first and second devices 100, 200", what is meant is the location of one of the first and second devices 100, 200 with respect to the other of the first and second devices 100, 200.

The location may correspond in the field of the present invention to a positioning and/or to a particular orientation of one of the first and second devices 100, 200 with respect to the other of the first and second devices 100, 200.

Thus, by establishing a plurality of relative locations between the first and second devices 100, 200 at different times, it is possible to track the movement of one of the first and second devices 100, 200 with respect to the other of the first and second devices 100, 200.

In FIG. 1, the first device 100 comprises an oscillator 101, a time counter 102 clocked by the oscillator 101 of the first device 100, and a radiocommunication module 103.

In FIG. 2, the second device 200 comprises an oscillator 201, a time counter 202 clocked by the oscillator 201 of the second device 200, and a radiocommunication module 203.

By "oscillator" 101, 201, what is meant is an electronic component the function of which is to produce a periodic signal intended to clock other electronic components, such as, for example, a time counter, a frequency synthesizer, etc.

By "time counter" 102, 202, what is meant is an electronic component the function of which is to deliver a timestamp. The clocking of a time counter is implemented by the oscillator to which it is connected. For example, the time counter 102 of the first device 100 comprises a clock input clk_1 that is connected to a clock output S1 of the oscillator 101 of the first device 100 (FIG. 1). For example, the time counter 202 of the second device 200 comprises a clock input clk_2 that is connected to a clock output S2 of the oscillator 201 of the second device 200 (FIG. 2). For example, the clock inputs allow pulses to be counted to be delivered in the context of time counters.

By "timestamp" what is meant is a datum that allows a piece of temporal information to be associated with an event. Generally, a timestamp may represent an amount of time passed since a reference time, or even a time and date.

Of course, the radiocommunication modules 103, 203 are configured so as to enter into communication wirelessly in order to exchange data. A radiocommunication module in the sense of the present description is therefore a radioelectric-wave transceiver module.

Preferably, the magnetic locating system is such that one of the first and second devices 100, 200 is able to move with respect to the other of the first and second devices 100, 200. Moreover, there is no wired communication link between the first and second devices 100, 200.

Moreover, the magnetic locating system also comprises the device 104, 204 for emitting and receiving alternating magnetic fields, which device is connected to the oscillators 101, 201 of the first and second devices 100, 200. This emitting and receiving device 104, 204 is configured to allow a propagation of alternating magnetic fields between the first device 100 and the second device 200, notably in order to implement at least one step of finding a relative magnetic location between the first device 100 and the second device 200 while taking into account data from the emitting and receiving device 104, 204 as will be described below. This device 104, 204 for emitting and receiving alternating magnetic fields is notably formed of two parts one of which is integrated into the first device 100 and the other of which is integrated into the second device 200. These parts may be formed by an emitter 104 of alternating magnetic fields and a receiver 204 of alternating magnetic fields, respectively. The emitter 104 of alternating magnetic fields may be clocked by one of the oscillators (that of the first device 100 in the example illustrated in FIG. 1) and the receiver 204 of alternating magnetic fields may then be clocked by the other of the oscillators (that of the second device 200 in the example illustrated in FIG. 2). It will therefore be understood that there is a synchronization problem to be solved if it is desired to improve the operation of the magnetic locating system since the emitter 104 and the receiver 204 will be clocked by different oscillators.

The emitter 104 of alternating magnetic fields may comprise frequency synthesizers 104a, 104b, 104c, also called direct digital synthesizers (DDS). Each frequency synthesizer 104a, 104b, 104c of the emitter 104 of alternating magnetic fields may comprise a clock input clk_3 connected to the clock output S1 of the oscillator 101 of the first device 100, a setpoint C1 input En1 specifying thereto at which frequency it must operate, and an input En2 that is intended to receive a start-up order O1. For the sake of clarity of FIG. 1, only the setpoint C1 input En1, the start-up order O1 input En2 and the clock input clk_3 of the frequency synthesizer 104a have been shown, but the same principle applies to the other frequency synthesizers 104b, 104c. Each frequency synthesizer 104a, 104b, 104c drives a coil 105a, 105b, 105c of the emitter 104, which coil is intended to generate a corresponding alternating magnetic field with suitable driving of the associated frequency synthesizer. In other words, each coil 105a, 105b, 105c is excited with a frequency that is specific thereto by a frequency synthesizer 104a, 104b, 104c associated with said coil 105a, 105b, 105c.

The receiver 204 of alternating magnetic fields may comprise frequency synthesizers 204a, 204b, 204c. Each frequency synthesizer 204a, 204b, 204c of the receiver 204 of alternating magnetic fields may comprise a clock input clk_4 that is connected to the clock output S2 of the oscillator 201 of the second device 200, a setpoint C2 input En3 specifying thereto at which frequency it must operate, and an input En4 that is intended to receive a start-up order O2. Each frequency synthesizer 204a, 204b, 204c allows a reference modulation frequency, for example a phase and a quadrature, to be delivered to a unit 210 for demodulating the received alternating magnetic fields. This demodulating unit 210 is connected to coils 205a, 205b, 205c (called "receiving coils") of the receiver 204 of alternating magnetic fields, which coils are intended to capture/receive the corresponding alternating magnetic fields emitted by the coils of the emitter 104 of alternating magnetic fields. The phase and quadrature allow two pieces of information to be determined, namely the amplitude and phase of the signal demodulated on all of the receiving coils 205a, 205b, 205c. For each coil 205a, 205b, 205c of the receiver 204, a phase and a quadrature is provided for each frequency. Thus, for example, for a three-axis receiver receiving signals emitted by three coils 105a, 105b, 105c, there are nine phase-and-quadrature pairs to be used by the demodulating unit 210. Thus, the demodulating unit 210 allows detections that are synchronous in phase and in quadrature to be carried out in order to determine, on the end of the receiver 204 of alternating magnetic fields, the amplitudes and the phases of the received magnetic fields from information delivered by the frequency synthesizers 204a, 204b, 204c of the receiver 204 of alternating magnetic fields. For the sake of clarity of FIG. 2, only the setpoint C2 input En3, the start-up order O2 input En4 and the clock input clk_4 of the frequency synthesizer 104a are shown in FIG. 2, but the same principle applies to the other frequency synthesizers 204b, 204c.

The setpoints C1 are different for each frequency synthesizer 104a, 104b, 104c of the emitter 104 of alternating magnetic fields with the aim of differentiating the frequencies of the magnetic fields emitted by the various coils 105a, 105b, 105c of the emitter 104 of alternating magnetic fields. It will thus be understood that each setpoint C1 is different from the other setpoints C1. Moreover, each setpoint C2 is identical to one of the setpoints C1; the setpoints C1 may be chosen by the first device 100, and transmitted to the second device 200 by radiocommunication between the radiocommunication modules 103, 203 of the first and second devices 100, 200. It will thus be understood that each setpoint C2 is different from the other setpoints C2.

In FIGS. 1 and 2, an embodiment is shown in which the first device 100 comprises the emitter 104 of alternating magnetic fields, and in which the second device 200 comprises the receiver 204 of alternating magnetic fields. Although the inverse is possible, this embodiment is preferred because the receiver 204 of alternating magnetic fields (or more generally the second device 200) is generally movable implying that the second device 200 is more compact: therefore for example a power source and the reception of the alternating magnetic fields which consumes less power than the emission thereof, are incorporated therein.

The use of data relating to the received and emitted alternating magnetic fields to allow at least one relative magnetic location between the first and second devices 100, 200 to be generated will not be described in detail because known per se to those skilled in the art; for example such a use may be derived from patent application US 2005/0165297, or even from the article by RAAB et al. entitled "Magnetic Position and Orientation Tracking System" published in IEEE Transactions on Aerospace and Electronic Systems, Vol. AES-15, No. 5 in September 1979 pages 709 to 718.

Figure 3:
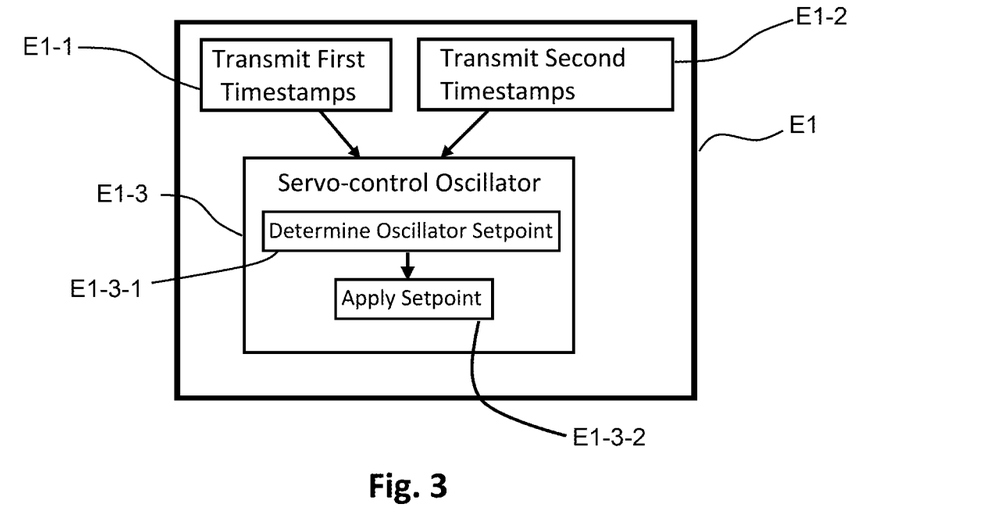
FIG. 3 illustrates one embodiment of a method for synchronizing the magnetic locating system.

As FIG. 3 shows, the method for synchronizing the magnetic locating system comprises a synchronization of the, i.e. a synchronizing step E1 configured to synchronize the, oscillators 101, 201 of the first and second devices 100, 200 by adjustment of the operation of the time counter 202 of the second device 200 to the operation of the time counter 102 of the first device 100. Notably, this adjustment is carried out by servo-controlling the oscillator 201 of the second device 200. By servo-controlling the oscillator 201 of the second device 200, what is meant is that its operation will be deliberately modified because of the sought-after adjustment between the time counters, whereas the oscillator 101 of the first device 100 will preferably remain at the same operating frequency: the frequency of the oscillator 201 may be modified whereas that of the oscillator 101 is preferably not. The adjustment of the operation of one time counter to another allows the latter to tend to give, for a given time, timestamps that are similar/identical within an adequate residual offset, typically smaller than one microsecond. In particular, the stability of the synchronization may be such that the timestamp difference between the time counters 102, 202 of the first and second devices 100, 200 may be comprised between −100 ns and 100 ns (this depending on the resolution of the time counters or on the noise associated with the operation of the radiocommunication chips used in the radiocommunication modules to process the radiocommunications participating in the synchronization such as will be described below) when the synchronization is effective. By stability of the synchronization, what is meant is that it may be reproduced on each start-up of the magnetic locating system, and therefore on each synchronization of the oscillators that is carried out consecutively to said start-up. In other words, the adjustment of the operation of the time counter 202 of the second device 200 to the operation of the time counter 102 of the first device 100 makes it possible to make the time counters operate in the same time base (for example in date and in time) while synchronizing the oscillators, the corollary of this being that the synchronizing step is such that it allows the time counters to be made to operate in the same time base. Below, the time base of the oscillator 101 of the first device 100 is denoted b1 and the time base of the oscillator 201 of the second device 200 is denoted b2.

The synchronization is here a hardware synchronization because it acts directly on the operation of one of the oscillators. By choosing suitable components, the precision of the synchronization is made good enough for the sought-after magnetic locating application.

As a result of this synchronizing step E1 it is then possible to achieve a precise magnetic location because the magnetic locating system has first and second devices 100, 200 (one of which is notably to be located with respect to the other) the oscillators 101, 201 of which, used by the device 104, 204 for emitting and receiving alternating magnetic fields, are synchronized, and the time counters 102, 202 of which are adjusted to each other. In this regard, it is possible to control the time at which the device 104, 204 for emitting and receiving alternating magnetic fields starts up both emitter 104 end and receiver 204 end, and the operating frequency of the device 104, 204 for emitting and receiving alternating magnetic fields. In other words, the described adjustment has the advantage, on the one hand, of obtaining a dating system that is common to separate first and second devices 100, 200 each comprising its own time counter clocked by an associated oscillator, and, on the other hand, of synchronizing the oscillators (emitter end and receiver end) to operating frequencies, which results in the ability to implement a magnetic location by controlling the origin phase of alternating signals used to emit the alternating magnetic fields and the origin phase of alternating signals generated by the receiving coils: the limitation to within it is overcome. In emitter 104 end, the alternating signals are used to excite the coils 105a, 105b, 105c, which are called emitting coils, this resulting in the emission of the alternating magnetic fields. In receiver 204 end, the receiving coils 205a, 205b, 205c are excited by excitation fields from the emitted alternating magnetic fields, this resulting in the generation, for each receiving coil, of an alternating signal, in order to carry out the magnetic location. Thus, the synchronization in particular makes it possible to keep identical the phases and frequencies of the modulations of emitted alternating magnetic fields with reference signals serving for the demodulation of the received alternating magnetic fields. The reference signals are constructed in receiver 204 end using the oscillator 201 of the second device 200 synchronized to that of the first device 100: the same origin phase and the same frequency are then obtained for each of the first and second devices 100, 200. The reference signals allow the alternating signals generated by the receiving coils 205a, 205b, 205c to be decoded in order then to achieve, on the basis of the decoded data, the magnetic location. In this regard, a solution is proposed that allows the emission and the reception of the alternating magnetic fields to be carried out synchronously: the robustness of a wire solution is therefore obtained by controlling the emission and the reception of the alternating magnetic fields, while benefiting from the ergonomics/flexibility of use of a wireless solution.

Preferably, the radiocommunication modules 103, 203 are used to transmit data allowing participation in the synchronization since the first and second devices 100, 200 cannot communicate with each other via a wire link. In this regard, the synchronizing step E1 may comprise a step E1-1 of transmitting first timestamps $h1_{t_i}^{b1}$, determined by the time counter 102 of the first device 100, to the second device 200 by radiocommunication between the radiocommunication modules 103, 203 of the first and second devices 100, 200. The first timestamps are therefore transmitted to the radiocommunication module 203 of the second device 200 by the radiocommunication module 103 of the first device 100. In the notation $h1_{t_i}^{b1}$, is a positive integer higher than or equal to 1 and allowing the corresponding first timestamp to be identified, and b1 makes reference to the time base of the time counter 102 of the first device 100. As a result thereof, the second device 200 receives, notably successively and notably at regular intervals, the first timestamps $h1_{t_i}^{b1}$, which it will possibly use to servo-control its oscillator 201. The synchronizing step E1 also comprises a step E1-2 of determining second timestamps $h2_{t_i}^{b2}$ by the time counter 202 of the second device 200. In the notation $h2_{t_i}^{b2}$, i is a positive integer higher than or equal to 1 and allowing the corresponding second timestamp to be identified, and b2 makes reference to the time base of the time counter 202 of the second device 200. Moreover, the synchronizing step E1 furthermore comprises a step E1-3 of servo-controlling the oscillator 201 of the second device 200 using, i.e. taking into account, the first timestamps $h1_{t_i}^{b1}$, and the second timestamps $h2_{t_i}^{b2}$. This servo-controlling step E1-3 is implemented by the second device 200. In fact, the various first timestamps will possibly be used successively in association with the corresponding second timestamps to modify the operation of the oscillator 201 of the second device 200, for example by speeding it up or slowing it down, so as to tend to the obtainment of a common dating system and to the synchronization of the oscillators 101, 201 of the first and second devices 100, 200. Such a use of timestamps is advantageous because it allows the synchronization of the oscillators to be facilitated since the time counters are themselves clocked by said oscillators.

In this regard, the servo-controlling step E1-3 may be such that the operation of the oscillator 201 of the second device 200 will be modified to act on the clocking of the time counter 202 of the second device 200 in order to align the operation of said time counter 202 of the second device 200 with that of the first device 100, which will moreover result in the synchronization of the oscillators 101, 201 of the first and second devices 100, 200. According to one preferred example, the servo-controlling step E1-3 may comprise at least one, or more than one, step(s) E1-3-1 of determining a servo-control setpoint C3 (FIG. 2) of the oscillator 201 of the second device 200 each followed by a step E1-3-2 of applying said servo-control setpoint C3 to the oscillator 201 of the second device 200. Said, and where appropriate each, servo-control setpoint C3 is determined using a (i.e. on the basis of a) time differential δt (FIG. 2) taking into account one of the first timestamps (represented by the reference h1 in FIG. 2) and one of the second timestamps (represented by the reference h2 in FIG. 2). To generate the time differential δt, the second device 200 may comprise a differential generator 206 (FIG. 2) having as input two timestamps (here represented by h1 and h2) and generating as output the time differential denoted δt. The use of a time differential is advantageous in the sense that is it is a question of a datum that is simple to exploit in the context of the sought-after adjustment, notably implemented by servo-controlling one of the oscillators, preferably on the basis of a PI (proportional-integral) control law, to be sped up or slowed down. Thus, the synchronizing step may comprise a step of determining the time differential δt.

In the present description, generally, the—or each—servo-control setpoint is preferably determined so as to act on the timestamp deviation between the first and second time counters 102, 202. Notably, the—or each—servo-control setpoint is preferably determined so as to decrease the timestamp deviation between the first and second time counters 102, 202, or so as to keep the absolute value of this deviation below a predetermined threshold. The predetermined threshold is then chosen depending on the application for which it is considered that the oscillators 101, 201 of the first and second devices 100, 200 are synchronized.

It will be understood that the adjustment of the operation of the time counter 202 of the second device 200 to the operation of the time counter 102 of the first device 100 (and therefore in the end the synchronization of the oscillators 101, 201) may be implemented using a comparison of first and second timestamps $h1_{t_i}^{b1}$, $h2_{t_i}^{b2}$ that are related to each other. The idea is therefore here to determine one of the first timestamps $h1_{t_i}^{b1}$, according to the time base of the time counter 102 of the first device 100, and one of the second timestamps $h2_{t_i}^{b2}$, according to the time base of the time counter 202 of the second device 200, at times that are close or similar in order to be able to compare them in order to servo-control the operation of the oscillator 201 of the second device 200 via the aforementioned adjustment. An effective solution for implementing this idea proposes to use the fact that the transmission delay of a signal from the radiocommunication module 103 of the first device 100 to the radiocommunication module 203 of the second device 200, and the transition between a low level (0) and a high level (1) of this signal are sufficiently deterministic to allow a timestamp generated during the emission of a signal at the end of the first device 100 to be compared with a timestamp generated on the reception of the same signal at the end of the second device 200. This has the advantage of obtaining consistent values to be delivered as input in the context of servo-control of the oscillator of the second device 200.

It will thus be understood that it is preferably possible to associate a time of emission (FIG. 1) of a synchronization signal SYNC, by the radiocommunication module 103 of the first device 100, with one of the first timestamps $h1_{t_i}^{b1}$, and a time of reception (FIG. 2) of this synchronization signal SYNC, by the radiocommunication module 203 of the second device 200, with one of the second timestamps $h2_{t_i}^{b2}$, which will be able to be compared, subsequently, with said first timestamp $h1_{t_i}^{b1}$, in order to establish the time differential.

To be as precise as possible, it is preferable that, for each first timestamp $h1_{t_i}^{b1}$, the determination of said first timestamp $h1_{t_i}^{b1}$, is carried out on the emission of a corresponding synchronization signal SYNC, and that, for each second timestamp $h2_{t_i}^{b2}$, the determination of said second timestamp is carried out on the reception of a corresponding synchronization signal. In this regard, at the moment of the reception of a synchronization signal SYNC allowing one of the second timestamps $h2_{t_i}^{b2}$ to be determined, the second device 200 does not have the associated first timestamp $h1_{t_i}^{b1}$ to be compared with said one of the second timestamps $h2_{t_i}^{b2}$ to determine the aforementioned time differential δt. There is therefore a need to develop a mechanism allowing two timestamps corresponding to the emission of a signal by the first device 100 and to the reception of the same signal by the second device 200, respectively, to be taken into account to determine a corresponding time differential. The two timestamps that it is sought to compare are said to be "related" or to be "corresponding".

The following is the proposed solution to the need to develop this mechanism: the synchronizing step E1 may comprise the radiocommunication module 103 of the first device 100 emitting synchronization signals SYNC to the radiocommunication module 203 of the second device 200. These synchronization signals SYNC may be emitted at regular intervals, this allowing the convergence of the operation of the time counter 202 of the second device 200 to that of the first device 100 to be improved. Here, each of the first timestamps $h1_{t_i}^{b1}$ is transmitted by one of the synchronization signals SYNC; the first timestamp to be transmitted may then be encapsulated in a data packet that the synchronization signal propagates from the radiocommunication module 103 of the first device 100 to the radiocommunication module 203 of the second device 200. Moreover, in FIG. 1, each time a synchronization signal SYNC is emitted by the radiocommunication module 103 of the first device 100:

one of the first timestamps $h1_{t_i}^{b1}$ to be transmitted by a synchronization signal consecutive to said emitted synchronization signal SYNC is determined by the time counter 102 of the first device 100, and one of the second timestamps $h2_{t_i}^{b2}$ is determined by the time counter 202 of the second device 200, on reception, by the radiocommunication module 203 of the second device 200, of said emitted synchronization signal SYNC.

Thus, the first and second timestamps $h1_{t_i}^{b1}$, $h2_{t_i}^{b2}$ are consistently determined while transmitting the first timestamps to the second device 200 with successively emitted synchronization signals in order that the latter be able to implement the servo-control of its oscillator 201. Thus, when one of the second timestamps $h2_{t_i}^{b2}$ is determined, it will possibly be compared to the related first timestamp $h1_{t_i}^{b1}$ when the latter is received by the reception of the synchronization signal consecutive to said emitted synchronization signal that caused said second timestamp to be determined. It will be understood from what has been described above that the emission of the synchronization signals allows the transmitting step E1-1, the step E1-2 of determining the second timestamps, and the determination of the first timestamps, which steps were described above, to be implemented.

By "synchronization signal consecutive to another", what is meant is the synchronization signal that arrives directly after without interposition of an intermediate synchronization signal. Moreover, by "synchronization signal preceding another synchronization signal", what is meant is the synchronization signal that arrives directly before without interposition of an intermediate synchronization signal.

By combining said proposed solution with the embodiment using the one or more servo-control setpoints C3, during the synchronizing step E1, each synchronization signal received by the radiocommunication module 203 of the second device 200, and for which the second device 200 has available one of the second timestamps $h2_{t_i}^{b2}$ determined by the time counter 202 of the second device 200 on the reception of a synchronization signal preceding said received synchronization signal SYNC, causes the implementation of one of the steps E1-3-1 of determining a servo-control setpoint C3 for which the time differential δt is obtained while taking into account one of the first timestamps h1 extracted from said received synchronization signal SYNC, and said second timestamp h2 determined by the time counter 202 of the second device 200 on the reception of said synchronization signal preceding said received synchronization signal SYNC. In other words, on the reception of the synchronization signal SYNC, the first timestamp that it comprises is extracted with a view to obtaining the time differential. This has the advantage of allowing a comparison of two timestamps corresponding to the emission and to the reception of the same synchronization signal, respectively.

Preferably, the servo-controlling step E1-3 may comprise (FIG. 3) steps E1-3-1 of determining a servo-control setpoint C3 of the oscillator 201 of the second device 200 each followed by a step E1-3-2 of applying said servo-control setpoint C3 to the oscillator 201 of the second device 200. Each servo-control setpoint is then determined using the time differential taking into account one of the first timestamps h1, also denoted $h1_{t_i}^{b1}$, and one of the second timestamps h2, also denoted $h2_{t_i}^{b2}$, corresponding to a timestamp of the emission and to a timestamp of the reception of the same synchronization signal SYNC, respectively. Comparable timestamp values to be used to tend toward the adjustment of the operation of the time counter 202 of the second device 200 to that of the first device 100 are obtained, which, in the end, will result in the synchronization of the oscillators 101, 201.

Preferably, each step E1-3-1 of determining a servo-control setpoint of the oscillator 201 of the second device 200 is triggered by the reception of one of the synchronization signals SYNC. This allows the operation of the time counter of the second device 200 to be more finely adjusted to that of the first device 100. Moreover, here the synchronization signals SYNC are emitted at regular intervals so as to allow the determined servo-control setpoint C3 to be applied between the reception of the synchronization signal that triggered the determination of said servo-control setpoint C3 and the reception of a synchronization signal consecutive to the signal that triggered the determination of said servo-control setpoint C3. In other words, each servo-control setpoint C3 is applied before the reception by the radiocommunication module 203 of a synchronization signal consecutive to the signal that triggered the determination of said servo-control setpoint C3. This makes it possible for the servo-control setpoint C3 to be applied before a new second timestamp is determined in order to take into account the application of the servo-control setpoint in the determination of a new servo-control setpoint.

Figure 4:
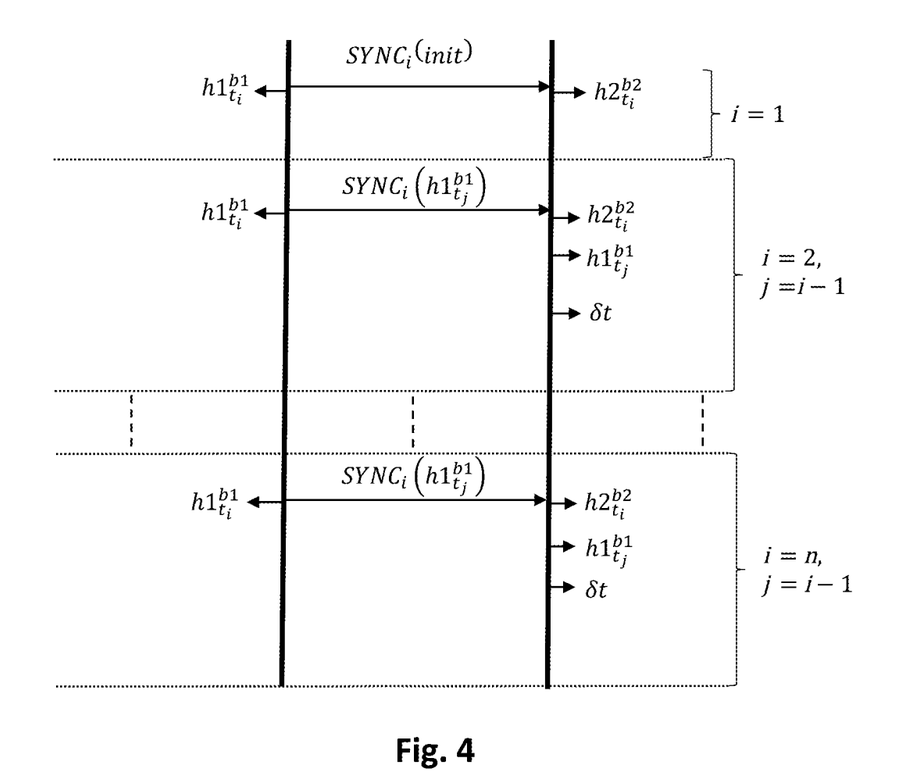
FIG. 4 illustrates, according to one embodiment, the operation of the first and second devices during the transmission of synchronization signals between the first and second devices.

It will be understood from what was described above that, to establish the time differential, the second device 200 must beforehand have available to it the second timestamp corresponding to the first timestamp extracted from the received synchronization signal so that said first and second timestamps correspond to those determined on the emission and on the reception of the same synchronization signal preceding said received synchronization signal. In this regard, it will be understood that the very first emitted synchronization signal will not contain any useful data, but will be sent in order to allow the generation of the very first of the first timestamps and of the very first of the second timestamps. Subsequently, the synchronization will be effective when the aforementioned time differential remains in a predetermined interval, for example between −100 ns and +100 ns. FIG. 4 schematically illustrates the operation of the emission and of the reception of the synchronization signals. Two vertical lines are shown in FIG. 4: what happens at the end of the first device 100 is shown to the left of the left-hand vertical line, what happens at the end of the second device 200 is shown to the right of the right-hand vertical line, and the synchronization signals are shown between the two vertical lines. In FIG. 4, the synchronizing step comprises, for i=1, the emission of a first synchronization signal denoted $SYNC_i$ (init) and allowing the initialization in the sense that its emission by the radiocommunication module 103 of the first device 100 allows an initial first timestamp $h1_{t_i}^{b1}$ to be determined, and in that its reception by the radiocommunication module 203 of the second device 200 allows an initial second timestamp $h2_{t_i}^{b2}$ to be determined. Next, taking i=2 and j=i−1, a cycle comprising an emission of a second synchronization signal $SYNC_j$ ($h1_{t_j}^{b1}$) containing the value $h1_{t_j}^{b1}$, and the emission of which by the radiocommunication module 103 of the first device 100 allows another first timestamp $h1_{t_i}^{b1}$ to be determined, and the reception of which by the radiocommunication module 203 of the second device 200 allows another second timestamp $h2_{t_i}^{b2}$ to be determined, is implemented. On the reception of $SYNC_j$ ($h1_{t_j}^{b1}$), the cycle is such that the second device 200 may extract the value of $h1_{t_j}^{b1}$ from the received synchronization signal, and may determine the time differential denoted δt taking into account $h1_{t_j}^{b1}$ and $h2_{t_j}^{b2}$, which are then available to it. This time differential δt may then be used to determine the servo-control setpoint C3 and to apply it to the oscillator 201 of the second device 200 (FIG. 2) before a new synchronization signal is received. Similarly, the synchronization may be continued by repeating the aforementioned cycle, notably with i able to range up to n, n being a positive integer depending on the number of iterations of the cycle. The value of n depends on the control law and should make it possible to combine a good precision for the synchronization and a transient (time taken to implement the synchronization) that is not too long in order not to penalize the magnetic locating application. Thus, n may be bounded depending on the application requirements: a transient of a few seconds at most, i.e. n possibly being equal to, or being of the order of, 1000, considering 200 iterations of the cycle per second.

According to one particular implementation, low-level signals generated by physical layers of the radiocommunication modules 103, 203 are used in the context of the determination of the first and second timestamps $h1_{t_i}^{b1}$, $h2_{t_i}^{b2}$. The physical layer is the first layer of the Open Systems Interconnection (OSI) model. The advantage of the use of these low-level signals is that they are closer to the physical signals: there is therefore little or no lag between the physical effect of emission, or of reception, of a signal, and the transit of the low-level signal, this allowing the sought-after stability of the synchronization of the oscillators to be ensured. In this regard, the radiocommunication modules 103, 203, may each comprise a physical layer, and:

for each emitted synchronization signal SYNC, the radiocommunication module 103 of the first device 100 generates a low-level signal IRQ_Tx (FIG. 1) when its physical layer emits the synchronization signal SYNC, this generation of the signal IRQ_Tx causing one of the first timestamps [[h1]]_(t_i)^b1 to be determined by the time counter 102 of the first device 100, and for each synchronization signal SYNC received by the radiocommunication module 203 of the second device 200, a low-level signal IRQ_Rx (FIG. 2) is generated by the physical layer of said radiocommunication module 203 of the second device 200, this generation of the signal IRQ_Rx causing one of the second timestamps $h2_{t_i}^{b2}$ to be determined by the time counter 202 of the second device 200.

Of course, it will be understood from all that has been described above that, preferably, as soon as one of the first timestamps is determined, the latter is transmitted to the radiocommunication module 103 of the first device 100 in order to subsequently be sent to the second device 200 via a corresponding synchronization signal.

The step E1-3 of servo-controlling the oscillator 201 of the second device 200 may comprise, as for example illustrated in the embodiment of FIG. 2, use of a loop filter 207. The role of the loop filter 207 is to generate each servo-control setpoint C3 of the second oscillator 201, the aim of which is to decrease the dating time differential between the time counters, or to keep its absolute value below a predetermined threshold in order to ensure the sought-after synchronization. Thus, the loop filter 107 receives as input the time differential, and delivers as output a servo-control setpoint C3 of the oscillator 201 of the second device 200. This predetermined threshold depends on the application;

for example, for a frequency of emitted sinusoidal signals of about 20 kHz, and a tolerated phase shift of plus or minus 1 degree, the predetermined threshold may be equal to 140 ns. In this regard, the loop filter 207 is said to provide feedback on the frequency of the oscillator 201 of the second device 200. For example, when the absolute value of the time differential is below the predetermined threshold, the synchronization of the oscillators 101, 201 is considered to be effective.

Each servo-control setpoint C3 may be a control voltage of the oscillator 201 of the second device 200. The oscillator 201 of the second device 200 may then be a voltage-controlled oscillator (VCO). The use of a voltage-controlled oscillator has the advantage of allowing a very fine granularity to be obtained in the frequency of the servo-controlled oscillator, and therefore in fine a very good stability in the frequency of the receiver 204, or where appropriate of the emitter 104, clocked by the servo-controlled oscillator. Preferably, it is the oscillator 201 of the second device 200 equipped with the receiver 204 that is servo-controlled because this for example allows, if the magnetic locating system comprises a plurality of second devices 201 each associated with a corresponding receiver 204, the oscillators connected to the receivers 204 to be easily synchronized to the same oscillator connected to the emitter 104.

Preferably, the loop filter 207 implements a proportional-integral, also denoted PI, control law that allows the regulation of the oscillator 201 of the second device 200 to be ensured via the successively determined and applied servo-control setpoints C3. Such a control law has the advantage of servo-controlling the phase and frequency of the servo-controlled oscillator, thus facilitating phase and frequency synchronization of the oscillators 101, 201 of the first and second devices 100, 200 in order to allow a subsequent control of the phase of the emitted and received alternating magnetic fields. Specifically, once the synchronization has been obtained, both the frequency and the phase of the receiver 204 may be aligned with those of the emitter 104.

A time differential δt taking into account, or obtained while taking into account, one of the first timestamps $h1_{t_i}^{b1}$ and one of the second timestamps $h2_{t_i}^{b2}$ was mentioned above. This time differential δt may be determined via a step of determining the time differential during the synchronizing step E1. This time differential δt may be a differential between said one of the first timestamps $h1_{t_i}^{b1}$ and said one of the second timestamps $h2_{t_i}^{b2}$, the differential may then be obtained by subtracting said one of the second timestamps $h2_{t_i}^{b2}$ from said one of the first timestamps $h1_{t_i}^{b1}$, or vice versa. According to another embodiment, the time differential δt is said to also take into account an offset. Thus, the time differential δt may be obtained by subtracting, from said one of the first timestamps $h1_{t_i}^{b1}$, said corresponding one of the second timestamps $h2_{t_i}^{b2}$ and the offset. The advantage of taking into account the offset is to take into account the fact that there is a delay between the time of generation of said one of the first timestamps $h1_{t_i}^{b1}$ and of said one of the second timestamps $h2_{t_i}^{b2}$, this delay notably being due to the electronics used to allow the generation of these timestamps and to the propagation time of the signal between the radiocommunication modules 103, 203 (this propagation time may in contrast be considered to be negligible and not taken into account in the offset). In the context of magnetic location, this offset may be neglected because it generally remains constant. In the case where the offset is taken into account, the differential generator 206 of FIG. 2 may comprise an additional input (not shown) that delivers the offset to said differential generator 206.

Figure 5:
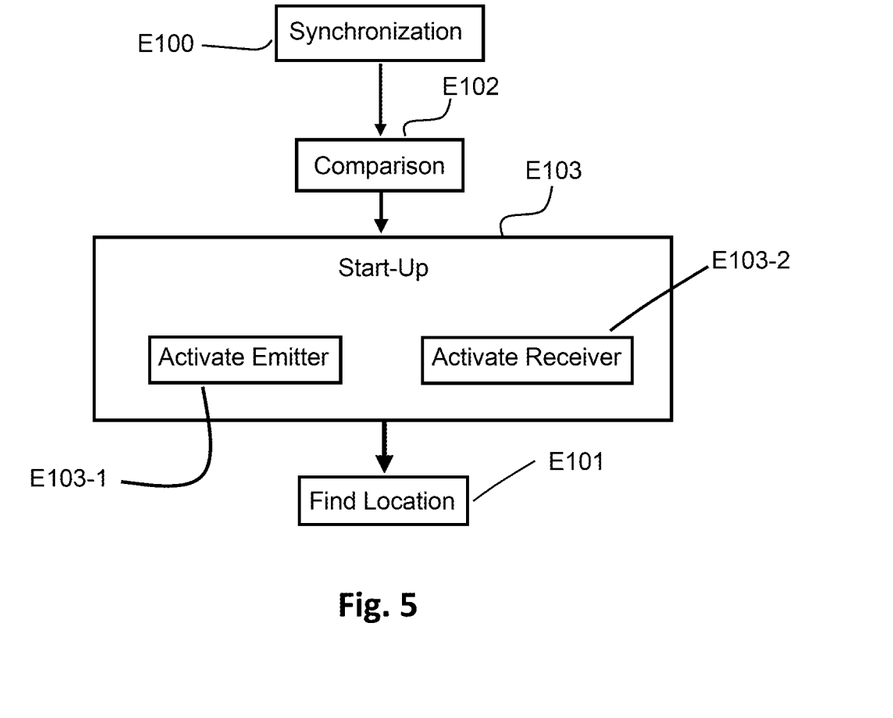
FIG. 5 illustrates one embodiment of a magnetic locating method.

As a result of all that was described above, the invention may also relate to a magnetic locating method, for example such as illustrated in the embodiment in FIG. 5, comprising a step E100 of implementing the synchronizing method such as described, and a step E101 of finding the relative location between the first and second devices 100, 200 while taking into account data from the device 104, 204 for emitting and receiving alternating magnetic fields. These data may for example be exploited in the way of the teaching of the article by RAAB et al. entitled "Magnetic Position and Orientation Tracking System" published in IEEE Transactions on Aerospace and Electronic Systems, Vol. AES-15, No. 5 in September 1979 pages 709 to 718. Notably, in order for the location to be as correct as possible, the location-finding step E101 is implemented once the oscillators have been synchronized. The advantages that result therefrom are due to those described above.

Thus, the magnetic locating method may comprise, as illustrated in FIGS. 1, 2 and 5, after adjustment of the operation of the time counter 202 of the second device 200 to the operation of the time counter 102 of the first device 100 (i.e. once the oscillators 101, 201 are synchronized), a step E102 of comparing a time setpoint C4 with data h3, h4 from the time counters 102, 202 of the first and second devices 100, 200. Moreover, the magnetic locating method may comprise a step E103 of starting up the device 104, 204 for emitting and receiving alternating magnetic fields, said step being triggered depending on the result of the comparing step E102. For example, the starting-up step E103 may be triggered once the time setpoint C4 is reached by the data h3 and h4: the time setpoint C4 corresponds, in this example, to a timestamp value. To implement the above, the first device 100 may comprise a comparator 106 receiving as input h3 and C4, and providing as output, where appropriate, the start-up order O1 transmitted to the En2 inputs of the frequency synthesizers 104a, 104b, 104c of the emitter 104. Similarly, the second device 200 may comprise a comparator 208 receiving as input h4 and C4 and providing as output, where appropriate, the start-up order O2 to be transmitted to the inputs En4 of the frequency synthesizers 204a, 204b, 204c of the receiver 204. In this regard, it will be understood that the use of a common dating system (time counters 102, 202 of the first and second devices 100, 200 adjusted to each other) allows the start-up of alternating signals for control of the emission of the alternating magnetic fields, and the start-up of the aforementioned reference signals at identical times, or times that differ by an acceptable tolerance, this resulting in a control of the origin phase of the emitted and received alternating magnetic fields: thus, the time difference between the times designated by the two origin phases is minimized. The time setpoint C4 may be chosen by the first device 100 and transmitted to the second device 200 by radiocommunication between the radiocommunication modules 103, 203 of the first and second devices 100, 200.

According to one implementation of the magnetic locating method (FIGS. 1, 2 and 5), the device 104, 204 for emitting and receiving alternating magnetic fields comprises the emitter 104 of alternating magnetic fields and the receiver 204 of alternating magnetic fields. Moreover, the magnetic locating method comprises, after synchronization of the oscillators 101, 201 of the first and second devices 100, 200:

a step E103-1 of activating the emitter 104 of alternating magnetic fields, the emitter 104 being clocked by one of the oscillators 101, 201 of the first and second devices 100, 200, this resulting in the emission of alternating magnetic fields, and a step E103-2 of activating the receiver 204 of alternating magnetic fields, the receiver 204 being clocked by the other of the oscillators 101, 201 of the first and second devices 100, 200, this resulting in the reception of the emitted alternating magnetic fields, the steps of activating the receiver 204 and emitter 104 of alternating magnetic fields being triggered (aforementioned step E103) simultaneously using the time setpoint C4 compared (aforementioned step E102), on the one hand, to the output data h3 of the time counter 102 of the first device 100, and, on the other hand, to the output data h4 of the time counter 202 of the second device 200. Notably, the activating steps are triggered when h3 and h4 reach the time setpoint C4. This allows the phase references used for the detection of the alternating magnetic fields at the level of the receiver 204 to be controlled with a high precision. Thus, it is possible to obtain a precise measurement of the phase of the received magnetic fields (via synchronous phase/quadrature detection for example) and to continue to be able to exploit, where appropriate, methods for detecting, or even compensating for, artefacts.

It results from what was described above that the location-finding step E101 is notably implemented after the step of starting up the emitting and receiving device 104, 204, or, where appropriate, after the steps of activating the receiver 204 and emitter 104.

Preferably, the synchronizing step E1 is triggered before the emitter 104 of alternating magnetic fields and the receiver 204 of alternating magnetic fields are activated, and is kept active during the operation of the emitter 104 of alternating magnetic fields and of the receiver 204 of alternating magnetic fields. This has the advantage of preserving a synchronization during the location, and not only at the moment of its start-up in order to prevent effects of drift of the phase for as long as exchanges between the radiocommunication modules are maintained.

It results from all that was described above that the invention also relates to a magnetic locating system in particular such as described above and suitable for the synchronizing method and/or for the locating method such as described above. In this regard, the magnetic locating system may comprise program-code instructions for the execution of the steps of the synchronizing method and/or of the magnetic locating method such as described.

In other words, apart from all that was described above with reference to the magnetic locating system, the latter may be configured so as to allow a synchronization of the oscillators 101, 201 of the first and second devices 100, 200 by adjustment, by servo-controlling the oscillator 201 of the second device 200, of the operation of the time counter 202 of the second device 200 to the operation of the time counter 102 of the first device 100. This has the advantage of allowing the aforementioned synchronization.

According to one particular implementation of the first device 100, the latter is configured to emit synchronization signals via its radiocommunication module 103 to the radiocommunication module 203 of the second device 200, and for each emitted synchronization signal, also called the current synchronization signal, the first device 100 is configured to:
  determine a first timestamp on the emission of said synchronization signal, and
  transmit said first timestamp to the radiocommunication module 203 of the second device 200 on the emission of a synchronization signal consecutive to said current synchronization signal.

According to one particular implementation of the second device 200 (as for example illustrated in FIG. 2), the latter comprises:
  the time-differential generator 206 configured to receive as input two timestamps and to establish said time differential while taking into account said two timestamps, and, where appropriate, the offset such as described above,
  the loop filter 207 configured to receive as input the time differential and to generate a servo-control setpoint C3 for servo-controlling the oscillator 201 of the second device 200, and
  a delay memory 209 connected to the time counter 202 of the second device 200 and to the time-differential generator 206, said delay memory 209 being configured to:
    receive a second timestamp $h2_{t_i}^{b2}$ determined by said time counter 202 on the reception of a synchronization signal by the radiocommunication module 203 of the second device 200, and
    transmit to the time-differential generator 206, if the delay memory 209 is storing a second timestamp h2 received beforehand, the second timestamp h2 stored in said memory 209 when the latter receives said determined second timestamp $h2_{t_i}^{b2}$.

Moreover, the radiocommunication module 203 of the second device 200 is configured to receive synchronization signals and to:
  extract a first timestamp h1 from at least a part of the received synchronization signals, and
  to transmit said extracted first timestamp h1 as input to the time-differential generator 206.

The interaction between a first device 100 and a second device 200 has been described. The magnetic locating system may comprise a plurality of second devices 200. Those skilled in the art will then be able to adapt the method for synchronizing the magnetic locating system in order to allow all the oscillators 201 of the second devices 200 to be synchronized to the oscillator 101 of the first device 100. This has the advantage of applying the present invention in the context of locating a plurality of second devices 200, each comprising a receiver 204 of alternating magnetic fields, with respect to the first device 100 comprising the emitter 104 of alternating magnetic fields.

The radiocommunication channel used to send the synchronization signals may also allow data, for example data relating to the received magnetic fields, to be sent to the part of the magnetic locating system that comprises the emitter of magnetic fields, in order to find the relative location between the first device and the second device. The communication channel may also allow data relating to instructions for starting up the magnetic locating device to be sent.

Apart from the advantages described above, the described synchronizing method, the described magnetic locating method, and the described magnetic locating system make it possible:
  via adjustment of the operation of the time counter 202 of the second device 200 to that of the first device 100, to preserve the flexibility of a wire solution even in the presence of two oscillators: this notably allows, within the locating system, a choice to be preserved as to the frequencies to be used by the emitter of alternating magnetic fields to generate the alternating magnetic fields, said emitter notably being integrated into the first device,
  to exploit possible phase differences between the reception and emission data of the alternating magnetic fields to detect, and optionally compensate for, artefacts such as, for example, magnetic-field perturbators—the phase ambiguity is then no longer limited to within π, and the location is therefore more precise, to obtain a tolerance in the time even if the communication channel between the radiocommunication modules is lost. Specifically, the servo-control setpoint controlling the oscillator of the second device then remains set to the last valid output of the control law: the oscillator remains at this frequency during the interruption, and when the communication channel becomes operational again, maintenance of the synchronizing step during the magnetic location allows the operation of the time counter and of the oscillator of the second device to be set once more to those of the first device, and to use a communication channel between the first and second devices that is already present in conventional magnetic locating systems: it is enough therefore to make the necessary modifications described above to implement the invention.

All that was said above with reference to the synchronizing method may be applied to the locating system, or to the magnetic locating method, and vice versa.

The synchronizing method, the locating method and the magnetic locating system described above may have an industrial application in the field of magnetic location in medicine. In particular, the magnetic locating system may have six degrees of freedom (in position and in angle) and may be used in the medical field, in which it is for example sought to track the movement of the second device 200 in a body with respect to the first device 100 located outside this body and notably stationary with respect to this body. In the example of application to the medical field, the first device 100 comprising the emitter 104 is stationary outside the body of a patient, and the second device 200 comprising the receiver 204 may move at the surface of the body or inside the body. Of course, the synchronizing and magnetic locating methods and the magnetic locating system may be used in any field implementing the use of a magnetic locating system.

Notably, during the use of the magnetic locating system, whether it be in the context of the synchronizing method or in the context of the magnetic locating method, the first device 100 remains at a distance from the second device 200 (for example smaller than one meter) that is suitable for the strength of the magnetic moment emitted by the emitter 104 and for the sensitivity of the receiver 204, in order to permit a suitable magnetic location: in other words, it is necessary for the emitted magnetic fields to be correctly received by the receiver 204. This has the advantage of limiting masking by third objects or operation over distances that are too large, which would result in the degradation of the performance of the synchronization and therefore of the magnetic location.

A magnetic locating system of six dimensions was mentioned above, the invention may also apply to any magnetic locating system of lesser dimension (for example a system of 5 dimensions, in the case where the receiver comprises only a single receiving coil and in which the angle according to the axis of the coil cannot be resolved).

The invention claimed is:

1. A magnetic locating method for finding a relative location between a first device and a second device of a magnetic locating system, wherein:

the first device and the second device each comprise an oscillator, a time counter clocked by said oscillator, and a radiocommunication module, the first device further comprises a magnetic emitter configured to emit alternating magnetic fields, the second device further comprises a magnetic receiver configured to receive alternating magnetic fields emitted by the magnetic emitter, and the magnetic emitter and the magnetic receiver are connected to the oscillators of the first and second devices, respectively, the method comprising:

synchronizing the oscillators of the first and second devices by adjusting, by servo-controlling the oscillator of the second device thereby adjusting operation of the time counter of the second device to operation of the time counter of the first device, and locating the first and second devices relatively to each other while taking into account data from the magnetic emitter and the magnetic receiver.

2. The magnetic locating method according to claim 1, wherein the synchronizing comprises:

transmitting first timestamps, determined by the time counter of the first device, to the second device by radiocommunication between the radiocommunication modules of the first and second devices, determining second timestamps by the time counter of the second device, and servo-controlling the oscillator of the second device using the first timestamps and the second timestamps.

3. The magnetic locating method according to claim 2, wherein the synchronizing comprises the radiocommunication module of the first device transmitting the first timestamps to the radiocommunication module of the second device using synchronization signals, each of the first timestamps being transmitted by one of the synchronization signals, and wherein each time a synchronization signal is emitted by the radiocommunication module of the first device:

one of the first timestamps to be transmitted by a synchronization signal consecutive to said emitted synchronization signal is determined by the time counter of the first device, and one of the second timestamps is determined by the time counter of the second device, on reception, by the radiocommunication module of the second device, of said emitted synchronization signal.

4. The magnetic locating method according to claim 2, wherein the servo-controlling comprises one or more steps, each step to determine a respective servo-control setpoint of the oscillator of the second device, each step followed by applying said respective servo-control setpoint, each servo-control setpoint being determined using a time differential taking into account one of the first timestamps and one of the second timestamps.

5. The magnetic locating method according to claim 3, wherein the servo-controlling comprises one or more steps, each step to determine a respective servo-control setpoint of the oscillator of the second device, each step followed by applying said respective servo-control setpoint, each servo-control setpoint being determined using a time differential taking into account one of the first timestamps and one of the second timestamps.

6. The magnetic locating method according to claim 5, wherein each step of determining a respective servo-control setpoint of the oscillator of the second device is triggered by reception of one of the synchronization signals, and wherein the synchronization signals are emitted at regular intervals so as to allow the application of the respective servo-control setpoint between the reception of the synchronization signal that triggered its determination and reception of a consecutive synchronization signal.

7. The magnetic locating method according to claim 5, wherein each synchronization signal received by the radiocommunication module of the second device, and for which the second device has available one of the second timestamps determined by the time counter of the second device on the reception of a synchronization signal preceding said received synchronization signal, causes the implementation of one of the steps of determining a respective servo-control setpoint for which the time differential is obtained while taking into account:
  one of the first timestamps, which is extracted from said received synchronization signal, and
  said second timestamp determined by the time counter of the second device on the reception of said synchronization signal preceding said received synchronization signal.

8. The magnetic locating method according to claim 2, wherein servo-controlling the oscillator of the second device comprises use of a loop filter.

9. The magnetic locating method according to claim 8, wherein the loop filter implements a proportional-integral control law.

10. The magnetic locating method according to claim 4, wherein each servo-control setpoint is a control voltage of the oscillator of the second device.

11. The magnetic locating method according to claim 1, comprising:
  after adjustment of the operation of the time counter of the second device to the operation of the time counter of the first device, comparing a time setpoint with data from the time counters of the first and second devices, and
  starting up the magnetic emitter and magnetic receiver, the starting up being triggered depending on a result of the comparing.

12. The magnetic locating method according to claim 1, further comprising, after synchronization of the oscillators of the first and second devices:
  activating the magnetic emitter, said magnetic emitter being clocked by the oscillator of the first device, resulting in the emission of alternating magnetic fields, and
  activating the magnetic receiver, said magnetic receiver being clocked by the oscillator of the second device, resulting in the reception of the emitted alternating magnetic fields,
  activating the magnetic receiver and activating the magnetic emitter being triggered simultaneously using a time setpoint compared to an output datum of the time counter of the first device, and to an output datum of the time counter of the second device.

13. The magnetic locating method according to claim 12, wherein the synchronizing is triggered before the magnetic emitter and magnetic receiver are activated, and is kept active during operation of the magnetic emitter and magnetic receiver.

14. The magnetic locating method according to claim 3, wherein one of the synchronization signals is received by the radiocommunication module of the second device, and wherein the second device has available one of the second timestamps determined by the time counter of the second device on the reception of a synchronization signal preceding said one synchronization signal, causes implementation of one of the steps of determining a respective servo-control setpoint for which a time differential is obtained while taking into account:
  one of the first timestamps, which is extracted from said one synchronization signal, and
  said second timestamp determined by the time counter of the second device on the reception of said synchronization signal preceding said one synchronization signal.

15. The method according to claim 1, wherein finding the relative location comprises using data from the time counters of the first and second devices.

16. A magnetic locating system comprising:
  a first device and a second device each comprising an oscillator, a time counter clocked by said oscillator, and a radiocommunication module, and
  a magnetic emitter and a magnetic receiver configured to emit and receive alternating magnetic fields, respectively, propagated between the first and second devices, said magnetic emitter and magnetic receiver being connected to the oscillators of the first and second devices, respectively,
  wherein the system is configured to
  synchronize the oscillators of the first and second devices by servo-controlling the oscillator of the second device thereby adjusting operation of the time counter of the second device to operation of the time counter of the first device, and
  locate the first and second devices relatively to each other while taking into account data from the magnetic emitter and the magnetic receiver.

17. The magnetic locating system according to claim 16, wherein the system is configured to find a relative location between the first and second devices using data from the time counters of the first and second devices.

* * * * *